(12) United States Patent
Qiu et al.

(10) Patent No.: US 11,744,459 B1
(45) Date of Patent: Sep. 5, 2023

(54) METHOD AND SYSTEM FOR DATA ANALYSIS OF RETINAL NERVE FIBROUS LAYER

(71) Applicant: JOINT SHANTOU INTERNATIONAL EYE CENTER OF SHANTOU UNIVERSITY AND THE CHINESE UNIVERSITY OF HONG KONG, Shantou (CN)

(72) Inventors: Kunliang Qiu, Shantou (CN); Mingzhi Zhang, Shantou (CN); Zhiqiang Guan, Shantou (CN)

(73) Assignee: JOUNT SHANTOU INTERNATIONAL EYE CENTER OF SHANTOU UNIVERSITY AND THE CHINESE UNIVERSITY OF HONG KONG, Shantou (CN)

( * ) Notice: Subject to any disclaimer, the term of this patent is extended or adjusted under 35 U.S.C. 154(b) by 0 days.

(21) Appl. No.: 18/123,564

(22) Filed: Mar. 20, 2023

(30) Foreign Application Priority Data

Mar. 22, 2022 (CN) .......................... 202210279317.8

(51) Int. Cl.
*A61B 3/12* (2006.01)
*A61B 3/10* (2006.01)
(Continued)

(52) U.S. Cl.
CPC .............. *A61B 3/12* (2013.01); *A61B 3/0025* (2013.01); *A61B 3/102* (2013.01); *A61B 3/1005* (2013.01);
(Continued)

(58) Field of Classification Search
CPC ....... A61B 3/12; A61B 3/0025; A61B 3/1005; A61B 3/102; A61B 3/14; G06T 7/0014;
(Continued)

(56) References Cited

U.S. PATENT DOCUMENTS

| 2005/0030475 A1* | 2/2005 | Zhou ..................... A61B 3/1005 351/215 |
| 2007/0216909 A1* | 9/2007 | Everett ................ A61B 5/0066 356/479 |

(Continued)

FOREIGN PATENT DOCUMENTS

| CN | 101400295 A | 4/2009 |
| CN | 111508606 A | 8/2020 |

(Continued)

*Primary Examiner* — Mohammed A Hasan

(57) ABSTRACT

Disclosed are a data analysis method and a data analysis system for retinal nerve fibrous layer. The method comprises the following steps: obtaining a peripapillary RNFL scanning image and a full-circumference RNFL thickness measurement data distribution image; obtaining a fundus scanning image, measuring a optic disc macular inclination angle; obtaining the upper and lower range of the RNFL scanning image, and measuring the upper and the lower RNFL thickness; obtaining an intersection position of an RNFL measuring ring and a blood vessel according to the canning image, and respectively correcting the upper and the lower RNFL thickness; performing a symmetry evaluation of the upper and the lower RNFL thickness according to the upper and the lower RNFL thickness correction value, and judging whether the RNFL data is abnormal. The system includes: image acquisition module, macular angle module, RNFL thickness module, RNFL thickness correction module and RNFL data evaluation module.

3 Claims, 10 Drawing Sheets

(51) Int. Cl.
*A61B 3/14* (2006.01)
*A61B 3/00* (2006.01)
*G06T 7/68* (2017.01)
*G06T 7/00* (2017.01)

(52) U.S. Cl.
CPC .............. *A61B 3/14* (2013.01); *G06T 7/0014* (2013.01); *G06T 7/68* (2017.01); *G06T 2207/10101* (2013.01); *G06T 2207/20021* (2013.01); *G06T 2207/30041* (2013.01); *G06T 2207/30101* (2013.01)

(58) Field of Classification Search
CPC ............. G06T 7/68; G06T 2207/10101; G06T 2207/20021; G06T 2207/30041; G06T 2207/30101
USPC ......................................................... 351/206
See application file for complete search history.

(56) References Cited

U.S. PATENT DOCUMENTS

| | | | |
|---|---|---|---|
| 2007/0263227 | A1* | 11/2007 | Mujat ..................... G06T 7/149 356/497 |
| 2009/0033868 | A1* | 2/2009 | Huang ................ A61B 3/1225 351/205 |
| 2009/0073387 | A1 | 3/2009 | Meyer |
| 2017/0169565 | A1 | 6/2017 | Huang |

FOREIGN PATENT DOCUMENTS

| | | |
|---|---|---|
| CN | 113177038 A | 7/2021 |
| JP | 2013116426 A | 6/2013 |
| JP | 2016152962 A | 8/2016 |

* cited by examiner

Obtaining a RNFL layered thickness measurement distribution image of the peripapillary scanning image;

Measuring a optic disc macular inclination angle based on the fundus scanning image;

Determining the upper range and the lower range of the OCT scanning image based on the optic disc macular inclination angle, and measuring the upper and the lower RNFL thickness;

Determining the retinal vascular thickness of the upper the lower range of the OCT measuring ring, and respectively correcting the upper and the lower RNFL thickness values;

Performing a symmetry evaluation of the upper RNFL thickness and the lower RNFL thickness according to the upper RNFL thickness correction value and the lower RNFL thickness correction value, and judging whether the RNFL data is abnormal.

FIG. 1

METHOD AND SYSTEM FOR DATA ANALYSIS OF RETINAL NERVE FIBROUS LAYER

CROSS-REFERENCE TO RELATED APPLICATIONS

This application claims priority to Chinese Patent Application No. 202210279317.8, filed on Mar. 22, 2022, the contents of which are hereby incorporated by reference.

TECHNICAL FIELD

The application belongs to the technical field of image measurement data processing, and particularly relates to a data analysis method and a data analysis system for retinal nerve fibrous layer.

BACKGROUND

At present, optical coherence tomography (OCT) is a common method for imaging retinal nerve fibre layer (RNFL). By scanning the retina in vivo, the retinal RNFL data are obtained, and the RNFL data are measured by algorithm, the abnormality of RNFL is evaluated, and then whether the thickness of RNFL is normal or not is judged, the method is helpful to the auxiliary diagnosis and monitoring of many diseases including glaucoma, multiple sclerosis, senile dementia and so on.

In the prior art, the main method for analyzing the thickness of RNFL data beside the peripapillary is to measure the average RNFL thickness of the full-circumference, four quadrants and 12 hour positions, and compare the values with the data of normal people, so as to judge whether the RNFL thickness of an individual is normal or not. However, due to some physical factors, the normal RNFL thickness distribution range of individuals is relatively large (for example, according to previous literature reports, the normal range of average RNFL thickness is 90 micron-120 micron), and the actual measured RNFL data of some actually normal individuals may also deviate from the normal value due to the influence of individual age, gender, eye axis length and other factors. In addition, because some individuals are in the early stage of illness, it is difficult to be accurately detected by current analysis methods (for example, the RNFL thickness of some individuals has dropped from 120 micron-100 micron, and it is still very likely that it cannot be correctly identified by the database) due to the early loss of the RNFL thickness data. To sum up, the current analysis methods of RNFL data have obvious limitations, which often leads to obvious false positive or false negative results, which is not conducive to clinical auxiliary diagnosis and condition change judgment of various ophthalmic diseases and nervous system diseases clinically.

SUMMARY

The application provides a method and a data analysis system for retinal nerve fibrous layer. By correcting the optic disc macular inclination angle, the peripapillary RNFL of an individual is divided into upper and lower halves, and by evaluating the thickness of the upper RNFL and lower RNFL respectively and comparing the symmetry of the thickness of the upper and lower RNFL of the same individual, the accuracy of early diagnosis of various diseases that affect the change of RNFL thickness is improved.

In order to achieve the above objective, the application provides the following scheme.

A data analysis method of retinal nerve fibrous layer, including the following steps:

obtaining a peripapillary RNFL scanning image and a full-circumference RNFL thickness measurement data distribution image by using an optical coherence tomography (OCT) equipment;

obtaining a fundus scanning image through a fundus photography equipment, measuring an optic disc macular inclination angle based on the fundus scanning image;

obtaining the upper range and the lower range of the RNFL scanning image based on the optic disc macular inclination angle and the full-circumference RNFL thickness measurement data distribution image, and respectively measuring the upper RNFL thickness and the lower RNFL thickness;

obtaining an intersection position of an RNFL measuring ring and a blood vessel according to the RNFL scanning image, and respectively correcting the upper RNFL thickness and the lower RNFL thickness according to a blood vessel thickness at the intersection position to obtain an upper RNFL thickness correction value and a lower RNFL thickness correction value;

performing a symmetry evaluation of the upper RNFL thickness and the lower RNFL thickness according to the upper RNFL thickness correction value and the lower RNFL thickness correction value, and judging whether the RNFL data is abnormal;

Optionally, obtaining the optic disc macular inclination angle according to the positions of the optic disc center and the macular center.

Optionally, dividing upper range and lower range of the RNFL scanning image according to the straight line between the optic disc and the central fovea of macula, and obtaining the upper range and the lower range of the RNFL scanning image.

Optionally, the correction formula of the upper RNFL thickness is as follows: corrected upper RNFL thickness=upper RNFL thickness-sum of the upper blood vessel thicknesses;

the correction formula of the lower RNFL thickness is as follows: corrected lower RNFL thickness=lower RNFL thickness-sum of the lower blood vessel thicknesses.

Optionally, symmetry score={1−(difference absolute value of corrected upper RNFL thickness and corrected lower RNFL thickness)/(average of corrected upper RNFL thickness and corrected lower RNFL thickness)}*100%;

whether the RNFL data is abnormal or not is judged according to the symmetry score.

Optionally, when the symmetry score is more than or equal to the preset value, the RNFL data are normal;

when the symmetry score is less than a preset value, the RNFL data are abnormal.

On the other hand, in order to achieve the above objectives, the application also provides a data analysis system for retinal nerve fibrous layer, which includes an image acquisition module, a macular angle module, an RNFL thickness module, an RNFL thickness correction module and an RNFL data evaluation module;

the image acquisition module is used for obtaining a peripapillary RNFL scanning image and a full-circumference RNFL thickness measurement data distribution image by using an optical coherence tomography (OCT) equipment;

the macular angle module is used for obtaining a fundus scanning image through a fundus photography equipment, measuring an optic disc macular inclination angle based on the fundus scanning image;

the RNFL thickness module is used for obtaining the upper range and the lower range of the RNFL scanning image based on the optic disc macular inclination angle and the full-circumference RNFL thickness measurement data distribution image, and respectively measuring the upper RNFL thickness and the lower RNFL thickness;

the RNFL thickness correction module is used for obtaining an intersection position of an RNFL measuring ring and a blood vessel according to the RNFL scanning image, and respectively correcting the upper RNFL thickness and the lower RNFL thickness according to a blood vessel thickness at the intersection position to obtain an upper RNFL thickness correction value and a lower RNFL thickness correction value;

the RNFL data evaluation module is used for performing a symmetry evaluation of the upper RNFL thickness and the lower RNFL thickness according to the upper RNFL thickness correction value and the lower RNFL thickness correction value, and judging whether the RNFL data is abnormal.

Optionally, the RNFL thickness module divides an upper range and a lower range of the RNFL scanning image according to the straight line between the optic disc and the central fovea of macula, and obtaining the upper range and the lower range of the RNFL scanning image.

Optionally, the RNFL thickness correction module includes an upper RNFL thickness correction unit and a lower RNFL thickness correction unit;

a correction formula of the upper RNFL thickness is preset in the upper RNFL thickness correction unit, and the correction formula of the upper RNFL thickness is as follows: corrected upper RNFL thickness=upper RNFL thickness-sum of the upper blood vessel thicknesses;

a correction formula of the lower RNFL thickness is preset in the lower RNFL thickness correction unit, and the correction formula of the lower RNFL thickness is as follows: corrected lower RNFL thickness=lower RNFL thickness-sum of the lower blood vessel thicknesses.

Optionally, the RNFL data evaluation module includes a symmetry evaluation unit, wherein a symmetry evaluation formula is preset in the symmetry evaluation unit;

the symmetry evaluation formula is as follows:

symmetry score={1−(difference absolute value of corrected upper RNFL thickness and corrected lower RNFL thickness)/(average of corrected upper RNFL thickness and corrected lower RNFL thickness)}*100%;

whether the RNFL data is abnormal or not is judged according to the symmetry score.

The application has the following beneficial effects.

The application discloses a method and a data analysis system for retinal nerve fibrous layer. By correcting the optic disc macular inclination angle, an individual's peripapillary RNFL is divided into an upper part and a lower part. The influencing factors among individuals are removed by respectively evaluating the RNFL thickness of the upper and lower part and comparing the symmetry of the RNFL thickness of the upper RNFL thickness and lower RNFL thickness of the same individual, which is more conducive to the early evaluation of abnormal RNFL thickness and can improve the early diagnosis accuracy of various diseases that affect the change of RNFL thickness.

BRIEF DESCRIPTION OF THE DRAWINGS

In order to explain the technical scheme of the application more clearly, the drawings needed in the embodiments are briefly introduced below. Obviously, the drawings in the following description are only some embodiments of the application. For ordinary technicians in the field, other drawings may be obtained according to these drawings without paying creative labor.

FIG. 1 is a flow chart of a data analysis method for retinal nerve fibrous layer according to Embodiment 1 of the present application;

FIG. 2A is the full-circumference RNFL measuring ring, FIG. 2B is the RNFL expansion image of the measuring ring, and FIG. 2C is the RNFL thickness measurement curve;

FIG. 4A is that the optical disc macular inclination angle is not considered in the prior art, and FIG. 4B is that the optical disc macular inclination angle is considered;

FIG. 5A is the full-circumference RNFL measuring ring, and FIG. 5B is the RNFL expansion image of the measuring ring.

DETAILED DESCRIPTION OF THE EMBODIMENTS

In the following, the technical scheme in the embodiment of the application will be clearly and completely described with reference to the drawings in the embodiment of the application. Obviously, the described embodiments are only a part of the embodiments of the application, but not the all embodiments. Based on the embodiments in this application, all other embodiments obtained by ordinary technicians in this field without creative work belong to the protection scope of this application.

In order to make the above-mentioned objectives, features and advantages of this application more obvious and easier to understand, the application will be further described in detail with the attached drawings and specific implementation methods.

Embodiment 1

FIG. 1 is a schematic flow chart of the data analysis method for retinal nerve fibrous layer according to Embodiment 1 of this application.

Figure 2A:
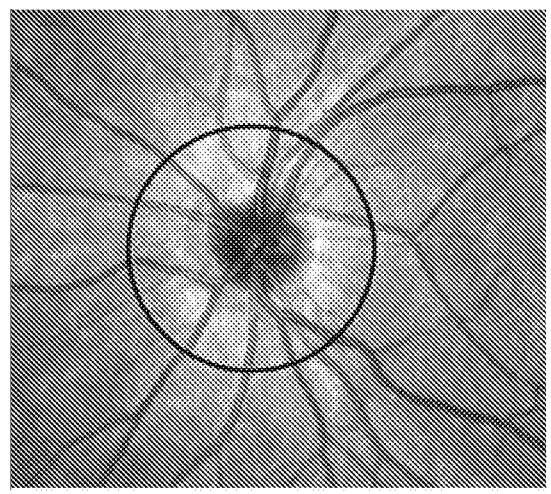
FIG. 2A, FIG. 2B and FIG. 2C are collectively area schematic diagrams of the distribution image of the peripapillary full-circumference RNFL thickness measurement data according to Embodiment 1 of the application, where
Figure 2B:
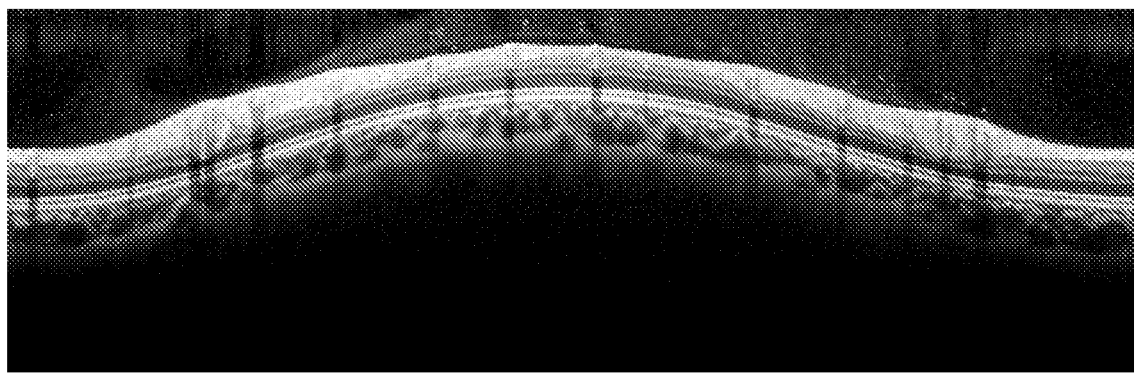
Figure 2C:
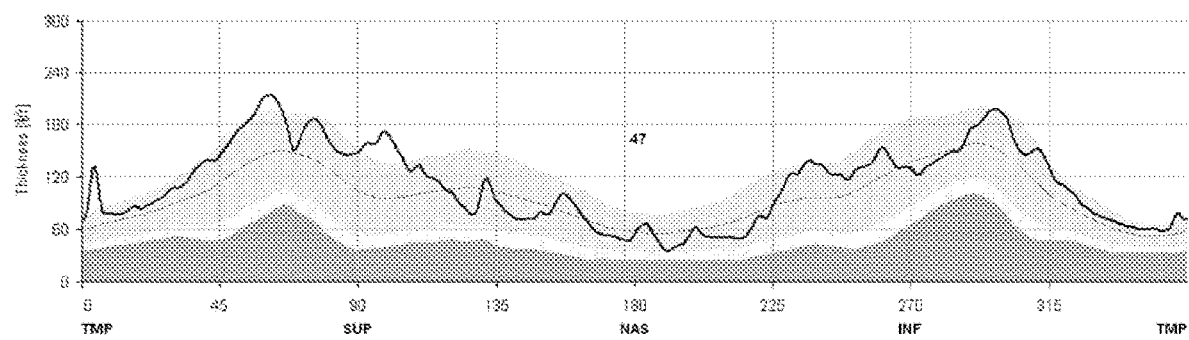

Firstly, the peripapillary RNFL scanning image and the full-circumference RNFL thickness measurement data distribution image are obtained by conventional OCT instruments, and the images are used to divide the upper and lower RNFL data in the following steps. FIG. 2A, FIG. 2B and FIG. 2C are the distribution images of the peripapillary full-circumference RNFL thickness measurement data: FIG. 2A shows the full-circumference RNFL measuring ring, FIG. 2B shows the RNFL expansion diagram of the measuring ring, and the uppermost high reflection signal in the diagram is the RNFL layer, and FIG. 2C shows the RNFL thickness measurement image, where the ordinate is the thickness in um, the abscissa is the position of each measurement point of the black measuring ring in degrees, and the black curve represents the full-circumference RNFL thickness measurement curve.

Figure 3:
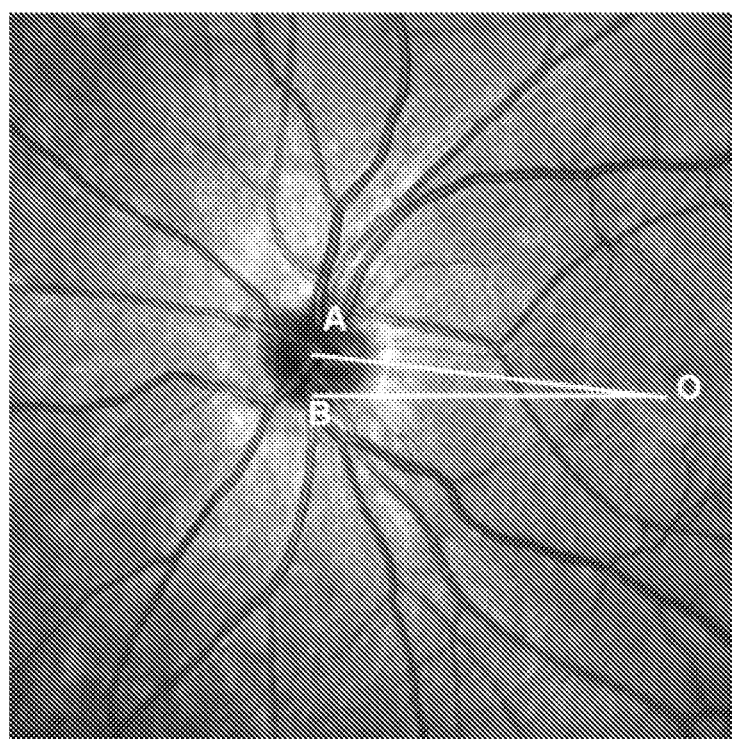
FIG. 3 is a schematic diagram of the optic disc macular inclination angle according to the first embodiment of the application, in which ∠AOB is the optic disc macular inclination angle.

Meanwhile, the fundus scanning image is obtained by fundus photography instrument, and the optical disc macular inclination angle is measured. As shown in FIG. 3, in this embodiment, taking two points of an optic disc center and a central fovea of macula as a straight line, wherein an angle formed by the straight line and a horizontal line is the optic disc macular inclination angle, named as ∠AOB.

Figure 4A:
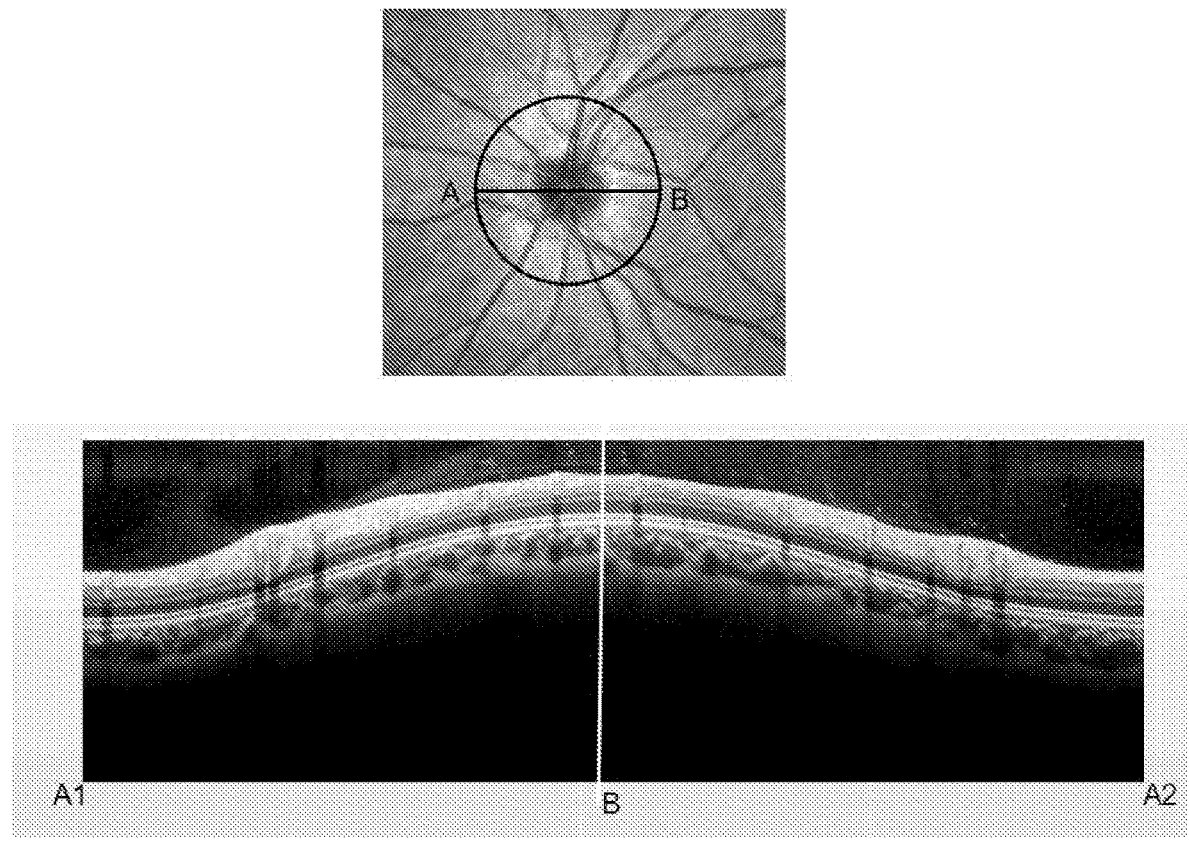
FIG. 4A and FIG. 4B are collectively a schematic diagrams of determining the upper and lower RNFL data distribution according to the optical disc macular inclination angle according to Embodiment 1 of the present application, where
Figure 4B:
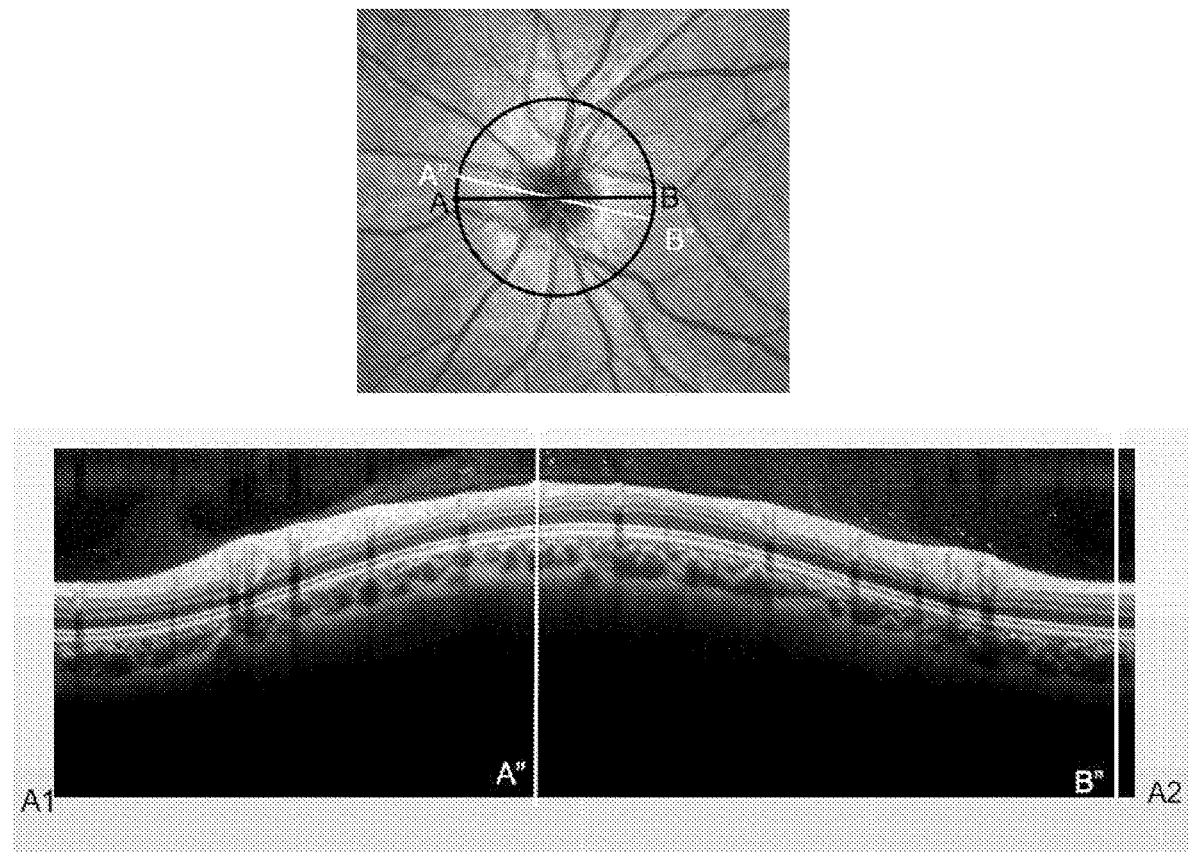

Then the specific ranges of upper and lower RNFL of the OCT scanning image are determined based on the optical disc macular inclination angle, and the thicknesses of the upper and lower RNFL are measured respectively. The upper and lower RNFL thickness measurements provided by the existing OCT instruments are all defined by horizontal lines, and then measured. However, according to the development and distribution of axonal bundles of retinal ganglion cells, the upper and lower RNFL data may be divided according to the position of the middle temporal suture. Considering that the position of the middle temporal suture may not be confirmed accurately and quickly in clinic at present, this technical scheme uses the straight line between the optic disc center and the central fovea of macular instead of the middle temporal suture to divide the upper and lower RNFL data. When the inclination angle of the peripapillary macula is 0°, the technical scheme of the embodiment of the application is consistent with the existing horizontal line division; however, in clinic, the optical disc macular inclination angle is not equal to 0 in most individuals. As shown in FIG. 4A and FIG. 4B, the distribution of upper and lower RNFL data is determined according to the optical disc macular inclination angle: FIG. 4A shows that in the prior art, the horizontal line (AB) is directly used as the dividing line between the upper and lower RNFL data without considering the optical disc macular inclination angle, where A1B is the upper RNFL data and BA2 is the lower RNFL data (note: A1 and A2 are the same point, both of which are points A of the black measuring ring). FIG. 4B shows the measurement of RNFL data considering the optical disc macular inclination angle (equivalent to the included angle between straight line AB and straight line A"B"). The lower RNFL data may be A" to B", while the upper RNFL data may be the sum of A2B" plus A1A".

Figure 5A:
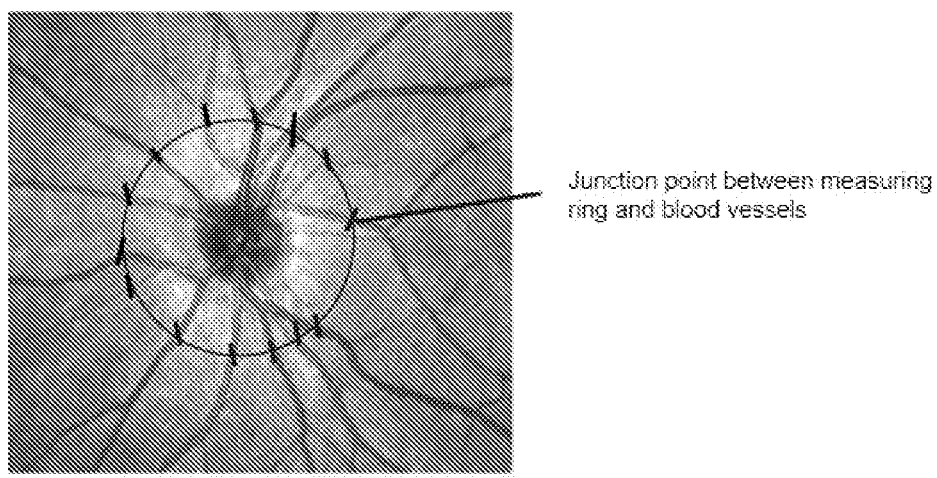
FIG. 5A and FIG. 5B are collectively a schematic diagrams of corrected blood vessel thickness versus RNFL thickness measurement data according to Embodiment 1 of the present application; where
Figure 5B:
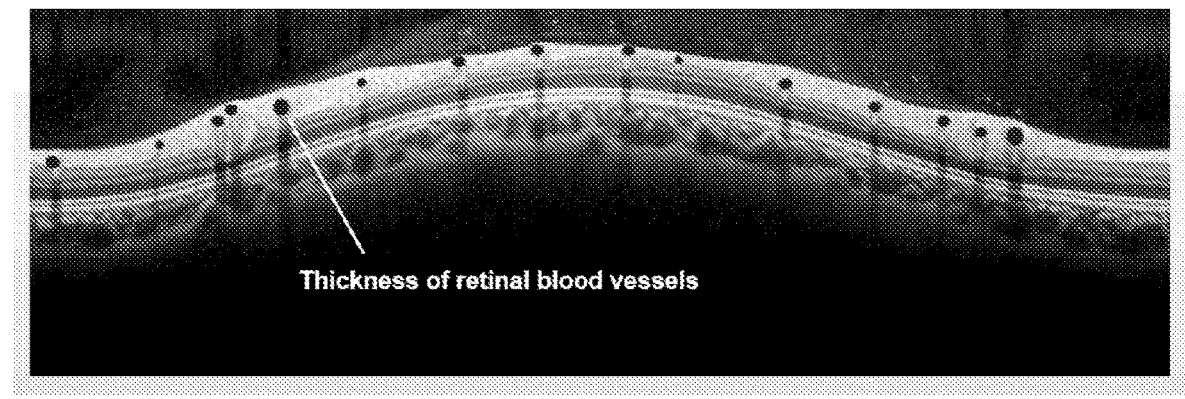

Then according to the existing optical disc scanning image of OCT, the intersection of RNFL measuring ring and blood vessel is determined, and the blood vessel thickness at the intersection is measured, so as to correct the RNFL thickness data. As shown in FIG. 5A and FIG. 5B, corrected blood vessel thickness versus RNFL thickness measurement data: intersection points of upper and lower blood vessels and OCT measuring ring (where the short black line segment is shown in FIG. 5A), and the blood vessel thickness (black solid dot part in part of image in FIG. 5B) is measured according to the characteristics of blood vessels on OCT scanning image. the correction formula of the upper RNFL thickness is as follows: corrected upper RNFL thickness=upper RNFL thickness-sum of the upper blood vessel thicknesses; the correction formula of the lower RNFL thickness is as follows: corrected lower RNFL thickness=lower RNFL thickness-sum of the lower blood vessel thicknesses.

Finally, the thickness symmetry of the upper and lower RNFL is analyzed according to the RNFL thickness correction value. The symmetry evaluation formula is as follows: symmetry score={1-(difference absolute value of corrected upper RNFL thickness and corrected lower RNFL thickness)/(average of corrected upper RNFL thickness and corrected lower RNFL thickness)}*100%. The closer the symmetry is to 100%, the higher the possibility that the RNFL data is normal. In this embodiment, the symmetry distribution interval of normal people (according to our current detection data of 30 normal people, the interval is 94% to 100%) is adopted, and if the symmetry of individuals is lower than 94%, it is judged as abnormal, indicating that the RNFL data is abnormal.

According to the technical scheme of the application, an individual's peripapillary RNFL is divided into an upper part and a lower part by correcting the optic disc macular inclination angle, and the influence factors among individuals are removed by respectively evaluating the thickness of the upper and lower RNFL and comparing the symmetry of the thickness of the upper and lower RNFL of the same individual, which is more conducive to the evaluation of early abnormal RNFL thickness and may improve the early diagnosis accuracy of various diseases that affect the change of RNFL thickness.

Embodiment 2

Figure 6:
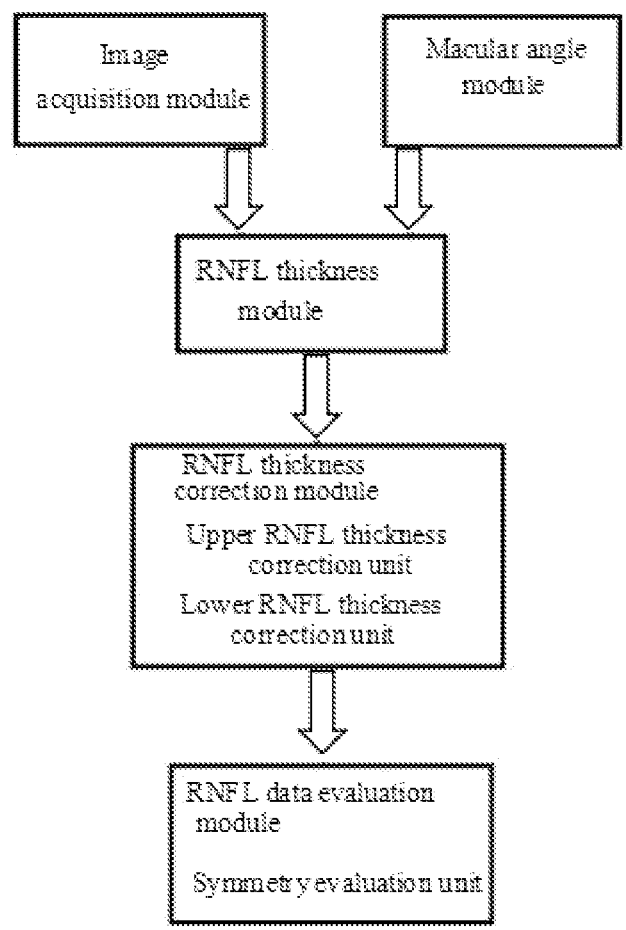
FIG. 6 is a schematic structural diagram of the data analysis system for retinal nerve fibrous layer according to Embodiment 2 of the present application.

FIG. 6 is a schematic structural diagram of the data analysis system for retinal nerve fibrous layer in Embodiment 2 of this application. The system mainly consists of an image acquisition module, a macular angle module, an RNFL thickness module, an RNFL thickness correction module and an RNFL data evaluation module.

Specifically, in this embodiment, the image acquisition module is used for obtaining a peripapillary RNFL scanning image and a full-circumference RNFL thickness measurement data distribution image by using an optical coherence tomography (OCT) equipment, and the images are used for dividing the upper and lower RNFL data in the subsequent steps.

The macula angle module is used for obtaining a fundus scanning image through a fundus photography equipment, measuring a optic disc macular inclination angle based on the fundus scanning image. In this embodiment, taking two points of a optic disc center and a central fovea of macula as a straight line, wherein an angle formed by the straight line and a horizontal line is the optic disc macular inclination angle (∠AOB).

The RNFL thickness module is used for obtaining the upper range and the lower range of the RNFL scanning image based on the optic disc macular inclination angle and the full-circumference RNFL thickness measurement data distribution image, and respectively measuring the upper RNFL thickness and the lower RNFL thickness. Specifically, the RNFL thickness module divides the upper and lower range of the RNFL scanning image according to straight line between the optic disc center and the central fovea of macular, so as to obtain the upper and lower ranges in the RNFL scanning image.

The RNFL thickness correction module is used for obtaining an intersection position of an RNFL measuring ring and a blood vessel according to the RNFL scanning image, and respectively correcting the upper RNFL thickness and the lower RNFL thickness according to a blood vessel thickness at the intersection position to obtain an upper RNFL thickness correction value and a lower RNFL thickness correction value. In this embodiment, the RNFL thickness correction module includes an upper RNFL thickness correction unit and a lower RNFL thickness correction unit. A correction formula of the upper RNFL thickness is preset in the upper RNFL thickness correction unit, and the correction formula of the upper RNFL thickness is as follows: corrected upper RNFL thickness=upper RNFL thickness-sum of the upper blood vessel thicknesses. A correction formula of the lower RNFL thickness is preset in the lower RNFL thickness correction unit, and the correction formula of the lower RNFL thickness is as follows: corrected lower RNFL thickness=lower RNFL thickness-sum of the lower blood vessel thicknesses.

The RNFL data evaluation module is used for performing a symmetry evaluation of the upper RNFL thickness and the lower RNFL thickness according to the upper RNFL thickness correction value and the lower RNFL thickness correction value, and judging whether the RNFL data is abnormal. The RNFL data evaluation module includes a symmetry evaluation unit, and a symmetry evaluation formula is preset in the symmetry evaluation unit; the symmetry evaluation formula is as follows: symmetry score={1−(difference absolute value of corrected upper RNFL thickness and corrected lower RNFL thickness)/(average of corrected upper RNFL thickness and corrected lower RNFL thickness)}*100%.

According to the symmetry score, whether the RNFL data is abnormal is judged. The closer the symmetry is to 100%, the higher the possibility that the RNFL data is normal. In this embodiment, the symmetry distribution interval of normal people (according to the current detection data of 30 normal people, this interval is 94% to 100%) is adopted. If the symmetry of individuals is lower than 94%, it is judged as abnormal, indicating that the RNFL data is abnormal.

The above-mentioned embodiment is only a description of the preferred mode of this application, not a limitation on the scope of this application. Without departing from the design spirit of this application, various modifications and improvements made by ordinary technicians in this field to the technical scheme of this application shall fall within the protection scope determined by the claims of this application.

What is claimed is:

1. A data analysis system for retinal nerve fibrous layer (RNFL), comprising an image acquisition module, a macular angle module, an RNFL thickness module, an RNFL thickness correction module and an RNFL data evaluation module;

wherein the image acquisition module is used for obtaining a peripapillary RNFL scanning image and a full-circumference RNFL thickness measurement data distribution image by using an optical coherence tomography (OCT) equipment;

the macular angle module is used for obtaining a fundus scanning image through a fundus photography equipment, measuring an optic disc macular inclination angle based on the fundus scanning image, taking two points of an optic disc center and a central fovea of macula as a straight line, wherein an angle formed by the straight line and a horizontal line is the optic disc macular inclination angle, the horizontal line is marked as AB, and the straight line between the optic disc center and the central fovea of macular is marked as A"B";

the RNFL thickness module is used for distributing the image based on the optic disc macular inclination angle and the full-circumference RNFL thickness measurement data, dividing an upper range and a lower range of the RNFL scanning image according to the straight line between the optic disc and the central fovea of macula, and obtaining the upper range and the lower range of the RNFL scanning image, wherein the lower range is a sum of two parts, A" to B plus B to B", and the upper range is a sum of two parts, A to A" plus B" to A, and measuring an upper RNFL thickness and a lower RNFL thickness respectively;

the RNFL thickness correction module is used for obtaining an intersection position of an RNFL measuring ring and a blood vessel according to the RNFL scanning image, and respectively correcting the upper RNFL thickness and the lower RNFL thickness according to a blood vessel thickness at the intersection position to obtain an upper RNFL thickness correction value and a lower RNFL thickness correction value; and the RNFL data evaluation module is used for performing a symmetry evaluation of the upper RNFL thickness and the lower RNFL thickness according to the upper RNFL thickness correction value and the lower RNFL thickness correction value, and judging whether the RNFL data is abnormal.

2. The data analysis system for retinal nerve fibrous layer (RNFL) according to claim 1, wherein the RNFL thickness correction module comprises an upper RNFL thickness correction unit and a lower RNFL thickness correction unit;

a correction formula of the upper RNFL thickness is preset in the upper RNFL thickness correction unit, and the correction formula of the upper RNFL thickness is as follows: corrected upper RNFL thickness=upper RNFL thickness-sum of the upper blood vessel thicknesses; and a correction formula of the lower RNFL thickness is preset in the lower RNFL thickness correction unit, and the correction formula of the lower RNFL thickness is as follows: corrected lower RNFL thickness=lower RNFL thickness-sum of the lower blood vessel thicknesses.

3. The data analysis system for retinal nerve fibrous layer (RNFL) according to claim 1, wherein the RNFL data evaluation module comprises a symmetry evaluation unit, a symmetry evaluation formula is preset in the symmetry evaluation unit;

the symmetry evaluation formula is:

a symmetry score={1−(difference absolute value of corrected upper RNFL thickness and corrected lower RNFL thickness)/(mean value of corrected upper RNFL thickness and corrected lower RNFL thickness)}*100%; and whether the RNFL data is abnormal or not is judged according to the symmetry score.

* * * * *